(12) United States Patent
Lee

(10) Patent No.: US 9,826,928 B2
(45) Date of Patent: Nov. 28, 2017

(54) APPARATUS AND METHOD FOR MEASURING THERMAL CONDUCTIVITY IN BURNS

(71) Applicant: CATHOLIC UNIVERSITY INDUSTRY ACADEMIC COOPERATION FOUNDATION, Seoul (KR)

(72) Inventor: Jun Yong Lee, Seoul (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 303 days.

(21) Appl. No.: 14/426,715

(22) PCT Filed: Dec. 24, 2014

(86) PCT No.: PCT/KR2014/012797
§ 371 (c)(1),
(2) Date: Mar. 6, 2015

(87) PCT Pub. No.: WO2015/099444
PCT Pub. Date: Jul. 2, 2015

(65) Prior Publication Data
US 2016/0256099 A1    Sep. 8, 2016

(30) Foreign Application Priority Data

Dec. 24, 2013 (KR) .................. 10-2013-0162376
Dec. 24, 2014 (KR) .................. 10-2014-0187910

(51) Int. Cl.
*G01K 11/12* (2006.01)
*A61B 5/00* (2006.01)
*G01N 25/18* (2006.01)

(52) U.S. Cl.
CPC .............. *A61B 5/445* (2013.01); *G01K 11/12* (2013.01); *G01N 25/18* (2013.01)

(58) Field of Classification Search
CPC ...................................................... G01K 11/12
See application file for complete search history.

(56) References Cited

U.S. PATENT DOCUMENTS 4,425,724 A * 1/1984 Scott .................. G09F 1/10
24/67.11
4,596,696 A * 6/1986 Scoville, Jr. .............. A61L 2/28
116/207

(Continued)

FOREIGN PATENT DOCUMENTS

EP         2402742 A2      1/2012
KR      10-0596703 B1      7/2006

OTHER PUBLICATIONS

Tatsukawa et al ("Development of Submillimeter Wave Catheter Transmitting a Gyrotron Output for Irradiation on Living Bodies", International Journal of Infrared and Millimeter Waves vol. 21 No. 8, 2000).*

(Continued)

*Primary Examiner* — Minh Phan
*Assistant Examiner* — Leon W Rhodes, Jr.
(74) *Attorney, Agent, or Firm* — Knobbe Martens Olson & Bear LLP

(57) ABSTRACT

There are provided an apparatus and method for measuring thermal conductivity capable of easily and accurately obtaining an extent of thermal damage of a targeted tissue. The apparatus for measuring thermal conductivity in burns includes a thermal paper stacking member having a plurality of sheets of thermal paper stacked thereon to form layers, and a pressing member configured to press the stacking member so that the thermal paper is stacked and maintained in a closely adhered state. Here, an extent of thermal damage (Continued)

of the targeted tissue according to the depth can be calculated as an extent of thermal damage of the stacking member according to the depth.

12 Claims, 7 Drawing Sheets

(56) References Cited

U.S. PATENT DOCUMENTS

| | | | | |
|---|---|---|---|---|
| 5,331,380 | A * | 7/1994 | Nasset | G03G 15/605 |
| | | | | 211/47 |
| 6,743,221 | B1 * | 6/2004 | Hobart | A61B 18/22 |
| | | | | 128/898 |
| 8,984,969 | B2 * | 3/2015 | Strunk | A61B 18/00 |
| | | | | 600/425 |
| 2002/0136261 | A1 | 9/2002 | Naka et al. | |
| 2005/0204574 | A1 * | 9/2005 | Bigelow, Jr. | B42F 13/12 |
| | | | | 33/623 |
| 2006/0122059 | A1 | 6/2006 | Mathur et al. | |
| 2007/0127543 | A1 | 6/2007 | Petrovic | |
| 2009/0153837 | A1 * | 6/2009 | Wang | G01J 1/4257 |
| | | | | 356/43 |
| 2011/0299719 | A1 * | 12/2011 | Podhajsky | A61B 34/10 |
| | | | | 382/100 |

OTHER PUBLICATIONS

International Search Report dated Apr. 8, 2015 of corresponding PCT Application No. PCT/KR2014/012797—4 pages.

* cited by examiner

APPARATUS AND METHOD FOR MEASURING THERMAL CONDUCTIVITY IN BURNS

TECHNICAL FIELD

The present invention relates to an apparatus and method for measuring thermal conductivity, and more particularly, to an apparatus and method for measuring thermal conductivity, which simply and intuitively display an actual heat transfer and a thermal distribution pattern in a skin burn of an animal or a human and can estimate an extent of thermal damage.

BACKGROUND ART

With a yearly increase in burn patients, it is essential to develop organized medical delivery systems for burn patients and materials for professional burn treatment, and secure medical facilities so as to reduce mortality caused by burns and minimize the financial and social loss caused by aftereffects of burns.

At present, however, burns are still classified into first to third degree burns according to visible and clinical aspects. For professional burn treatment, it is necessary to diagnose and classify burns in an accurate and detailed manner. This method forms the basis of research on developing specialized therapeutic methods so that the therapeutic methods can vary according to the extent or position of a burn.

As a method used to diagnose burns, Korean Registered Patent No. 10-0596703 discloses an apparatus for making a standardized model of burn wounds, which aids in accurate diagnosis and treatment of burns according to the extent or position of a burn by applying a proper level of heat to the skin of a subject so as to check an extent of burn injury.

Thermal damage of tissues starts when heat is transferred from any of various heat sources to the tissues. The heat transfer to such tissues is the first step of burning, and is a basic principle used to describe various kinds of burn characteristics and develop burn protection equipment or weapons. However, the heat transfer to such tissues is not visible to the naked eye, and there is no way to intuitively and easily measure the heat transfer. Thus, experiments conducted on animals, or simulation methods using physical and mathematical methods have been used as described above. These methods have a problem in that they are simulated using special programs depending on complicated mathematical formulas.

DISCLOSURE

Technical Problem

The present invention is designed to solve the problems of the prior art, and therefore it is an object of the present invention to provide an apparatus and method for measuring thermal conductivity, which is able to simply and intuitively display an actual heat transfer from a heat source to skin tissues and a thermal distribution pattern upon burning of the skin tissues.

It is another object of the present invention to provide an apparatus and method for measuring thermal conductivity, which is able to estimate an extent of thermal damage from various heat sources without using an animal.

Technical Solution

To solve the above problem of the prior art, according to an aspect of the present invention, there is provided an apparatus for measuring thermal conductivity in burns, which includes a plurality of sheets of thermal paper, a thermal paper stacking member having the thermal paper stacked thereon to form layers, and an upper plate having the stacking member loaded thereon. Here, the apparatus is able to measure an extent of burning in a state in which the thermal paper is stacked.

In this case, more preferably, the apparatus may include a pressing member configured to press the stacking member so that the thermal paper is stacked and maintained in a closely adhered state.

Also, more preferably, the stacking member may be stacked on the upper plate made of a heat-resistant silicone material.

In addition, more preferably, the upper plate may be formed on a plastically deformable lower plate.

Additionally, more preferably, adhesive oil may be applied between the sheets of thermal paper so that the stacking member closely adheres the thermal paper.

Further, more preferably, the adhesive oil may be at least one selected from the group consisting of oil and thermal grease.

Also, more preferably, the thermal paper may be K91HG-CE thermal paper.

In addition, more preferably, the pressing member may be selected from the group consisting of a magnetic material, a clip, a band, and a clamp.

Additionally, more preferably, the stacking member has reference holes formed therethrough to form reference points for three-dimensional (3D) modeling.

According to another aspect of the present invention, there is provided a method of measuring thermal conductivity, which includes a thermal paper stacking operation of determining a number of stacked sheets of thermal paper constituting a stacking member according to the thermal conductivity of a targeted tissue, a preparation operation of preparing the stacking member having the plurality of sheets of thermal paper stacked thereon to apply heat to the stacking member, a heating operation of applying heat to be tested to a top surface of the stacking member, and a thermal conductivity estimation operation of estimating thermal conductivity in the tissue by converting an extent of thermal damage according to a depth of the stacked thermal paper into an extent of thermal damage according to a depth of the targeted tissue. Here, the method is performed to obtain a thermal conduction process and a thermal distribution pattern in the targeted tissue.

In this case, more preferably, the preparation operation may include an upper plate temperature regulation operation of regulating a temperature of an upper plate configured to be placed below the stacking member to maintain a temperature similar to that of the targeted tissue, and a lower plate attachment operation of, when measurement of a curved surface is required, plastically deforming a lower plate so that the lower plate has the curved surface and attaching the upper plate to the lower plate.

Also, the method may further include a 3D reconstitution operation of three-dimensionally reconstituting a thermal image formed on the thermal paper piled as the respective layers of the stacking member after the heating operation of applying heat to be tested to the top surface of the stacking member.

In addition, more preferably, the number of stacked sheets of the thermal paper in the thermal paper stacking operation may satisfy the following Equation:

Number of stacked sheets of thermal paper=Thickness of tissue×$(k_p/k_d)/X_d$     Equation wherein kp represents a thermal conductivity constant of the thermal paper, kd represents a thermal conductivity constant of the tissue, and Xd represents a thickness of the thermal paper.

Further, more preferably, the thermal damage depth of the targeted tissue in the thermal conductivity estimation operation may satisfy the following Equation:

Thermal damage depth of targeted tissue=Number of sheets of thermal paper with discoloration×$Xd$× ($kd/kp$),    Equation wherein kp represents a thermal conductivity constant of the thermal paper, kd represents a thermal conductivity constant of the tissue, and Xd represents a thickness of the thermal paper.

Advantageous Effects

As described above, the apparatus and method for measuring thermal conductivity according to one embodiment of the present invention simply and intuitively displays an actual heat transfer and a thermal distribution pattern in a skin burn of an animal or a human, and thus can be useful in simply and accurately measuring thermal conductivity.

Also, the apparatus and method according to one embodiment of the present invention can be useful in obtaining accurate thermal conductivity and an extent of thermal damage in an animal or a human without performing an animal test.

Further, the apparatus and method according to one embodiment of the present invention can be useful in accurately estimating an extent of thermal damage in the tissue according to the depth through an arithmetical calculation based on the extent of thermal damage according to the thickness of the stacked thermal paper.

DESCRIPTION OF DRAWINGS

These and other features, aspects, and advantages of embodiments of the present invention will be more fully described in the following detailed description, taken accompanying drawings. In the drawings.

EMBODIMENTS

Hereinafter, the apparatus and method for measuring thermal conductivity according to embodiments of the present invention will be described in further detail with reference to the accompanying drawings.

Figure 1:
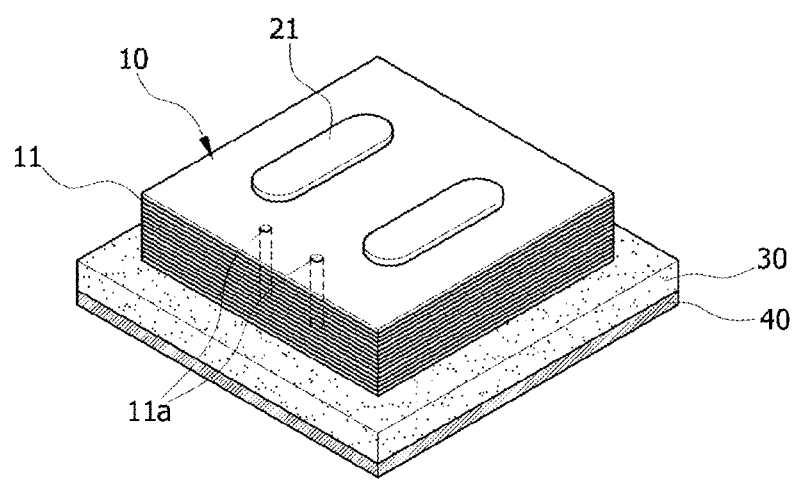
FIG. 1 is a perspective view showing an apparatus for measuring thermal conductivity according to a first embodiment of the present invention.
Figure 2:
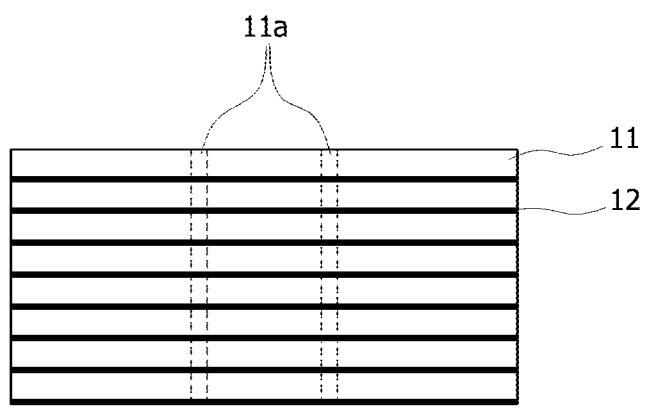
FIG. 2 is a cross-sectional view showing the stacking member shown in FIG. 1.
Figure 3:
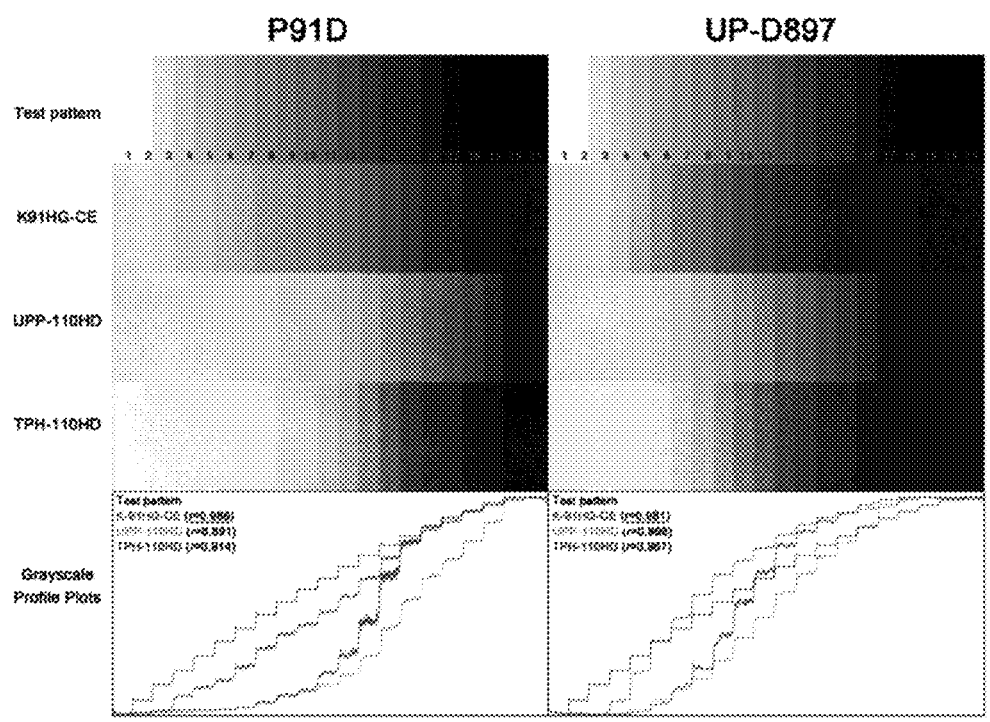
FIG. 3 is a diagram showing the analysis results of 21-level grayscale test pattern-printed products and grayscale profile plots.
Figure 4:
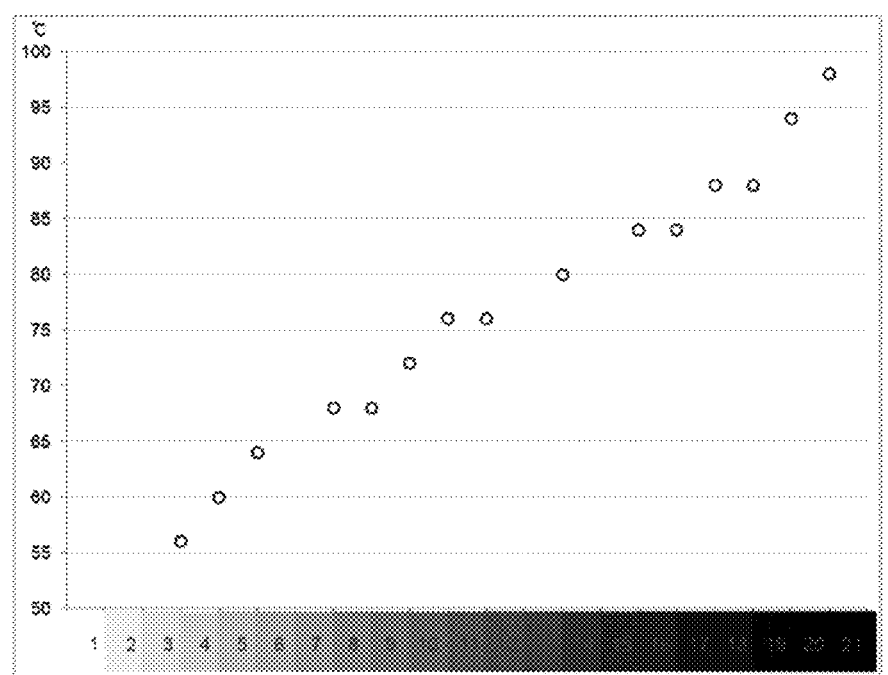
FIG. 4 is a diagram showing the analysis results of reaction temperatures of K91HG-CE thermal paper according to the respective gray scales.
Figure 5:
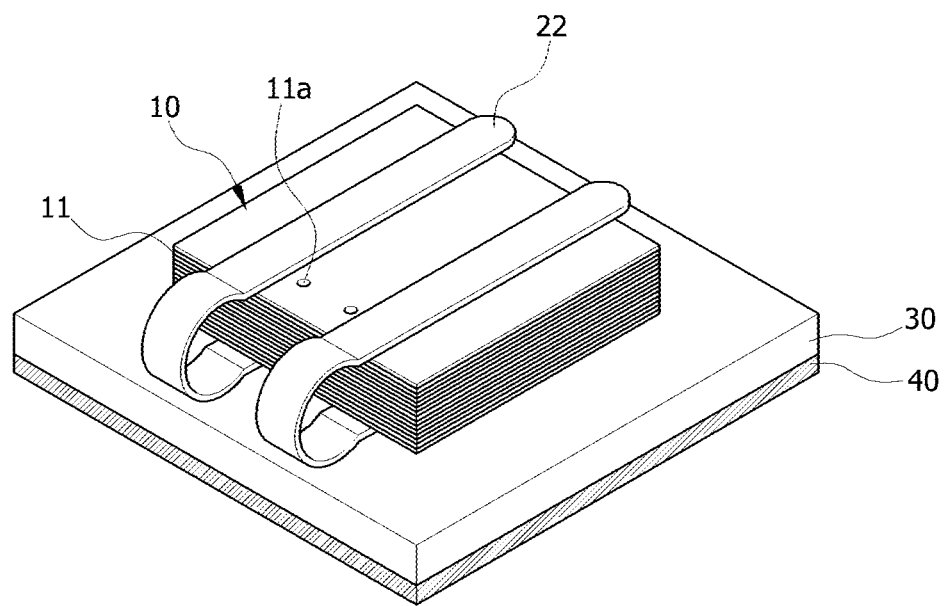
FIG. 5 is a perspective view showing an apparatus for measuring thermal conductivity according to a second embodiment of the present invention.
Figure 6:
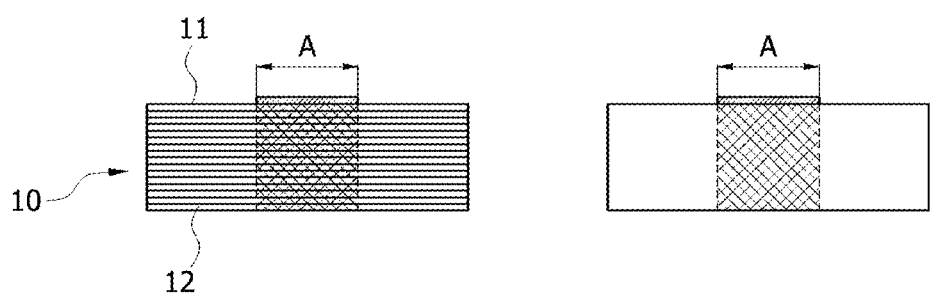
FIG. 6 is a state diagram schematically showing a thermal conductivity estimation operation.
Figure 7:
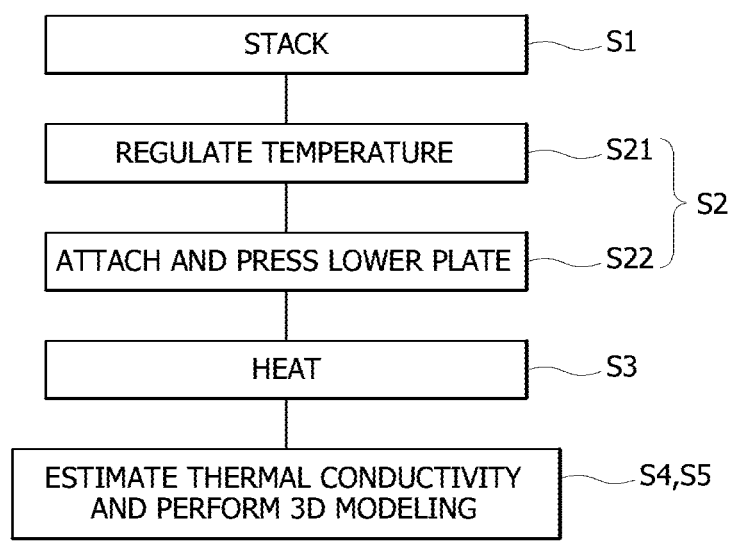
FIG. 7 is a flowchart illustrating a method of measuring thermal conductivity.

FIG. 1 is a perspective view showing an apparatus for measuring thermal conductivity according to a first embodiment of the present invention. FIG. 2 is a cross-sectional view showing the stacking member shown in FIG. 1. FIG. 3 is a diagram showing the analysis results of 21-level grayscale test pattern-printed products and grayscale profile plots to select thermal paper. FIG. 4 is a diagram showing the analysis results of reaction temperatures of K91HG-CE thermal paper according to the respective gray scales. FIG. 5 is a perspective view showing an apparatus for measuring thermal conductivity according to a second embodiment of the present invention. FIG. 6 is a state diagram schematically showing a thermal conductivity estimation operation, and FIG. 7 is a flowchart illustrating a method of measuring thermal conductivity.

As shown in FIGS. 1 to 2, the apparatus for measuring thermal conductivity according to one embodiment of the present invention includes a stacking member 10 having a plurality of sheets of thermal paper 11 stacked thereon, a pressing member 21 configured to press the stacking member 10, an upper plate 30 having the stacking member 10 loaded thereon, and a lower plate 40.

The stacking member 10 is configured to stack the plurality of sheets of thermal paper 11. The thermal paper 11 is special paper that reacts to heat. In this case, only a portion of the paper to which heat is applied turns black. The thermal paper is generally paper whose surfaces are coated with a thermal layer containing a chemical substance in which color develops when heat is applied to the paper. Therefore, heat may be used to simply record text or symbols. Generally, the thermal paper 11 is used as thermal printer paper or facsimile recording paper. According to a method of allowing two components to react and color to develop, a colorless leuco dye emitting electrons and a developer receiving the electrons are prepared in the form of fine granules, and applied onto the paper together with a binder. In this case, a degree to which color develops differs according to the temperature of heat applied to the paper. In addition to the thermal paper 11, paper with discoloration that is observable with the naked eye when heat is applied to the paper may also be used.

Meanwhile, in the present invention, the thermal paper is selected based on the following requirements to select the most preferable thermal paper. First, the thermal paper should have a thermal resolution capacity. That is, a temperature distribution of heat transferred to the thermal paper should be expressed by gray scales when a heat-sensitive material reacts sensitively to the heat. Therefore, when heat traces expressed on the thermal paper are observed later, the temperature distribution at that time may be calculated. Also, the gray scales expressed after the thermal reaction occurs should be retained even after a heat source is removed, which means that no inverse reaction should occur chemically. Second, the thermal paper should begin reacting when heat reaches a temperature that actually causes burns. When the thermal paper reacts to heat of a temperature that does not actually cause burns or only reacts to very high temperatures, utility of the thermal paper may be degraded. Third, the thermal paper should satisfy a stability requirement so that the thermal paper does not burn or melt at working temperatures.

Therefore, in the present invention, the following procedure is carried out to select the thermal paper capable of satisfying the above-described requirements.

Generally, thermal paper has been used in thermal printers to print text on receipts or faxed documents. However, typical thermal paper is used to print black and white text, and has a characteristic by which stronger colors develop when a temperature exceeds a certain temperature range. Therefore, it is difficult to determine a color development level according to the temperature, which means that the thermal resolution capacity is severely degraded, and in turn that the typical thermal paper is unsuitable for use as the thermal paper according to one embodiment of the present invention.

Therefore, a special thermal image printer which may be manufactured to print an image such as an ultrasonic image rather than the black and white letters to express certain gray scales is used to select the thermal paper. First, the gray scales are determined according to the proper temperature matching between the thermal image printer and the thermal paper, and the color development capacity of the thermal paper. Therefore, in the present invention, various types of thermal paper, for example K91HG-CE, UPP-110HD and TPH-110HD, are measured for thermal resolution capacity in various thermal image printers. In such a procedure, the thermal resolution capacity of the corresponding thermal paper may be evaluated by observing a pattern in which linear gray scaling from white to black reappears for 21-level grayscale test patterns. Therefore, in the present invention, the grayscale test patterns are classified according to various cases by means of combinations of the thermal image printers and the thermal paper, and the corresponding output is printed, and scanned to measure a grayscale profile. Thereafter, the corresponding profile is digitized to perform a bivariate correlation analysis.

FIG. 3 shows the analysis results of 21-level grayscale test pattern-printed products and grayscale profile plots to select thermal paper. Referring to the grayscale profile plot based on the analysis results, it can be seen that the K91HG-CE thermal paper has a pattern most similar a black stepped test pattern of the profile plot. While it may be assumed that it is most desirable to use thermal paper prepared or recommended by the corresponding image printer manufacturer when a certain image printer is determined, this is not always true in practice. Therefore, it could be seen that the above-described selection procedure of selecting the thermal paper according to one embodiment of the present invention is a very meaningful task. Therefore, based on the test result, the thermal paper having the most consistent thermal resolution capacity in the entire temperature range is judged to be K91HG-CE thermal paper, and the use of this thermal paper is judged to be the most desirable in the present invention.

Meanwhile, the reaction temperatures of the K91HG-CE thermal paper selected in the above-described test according to the respective gray scales are shown in FIG. 4. Referring to the corresponding drawing, it could be seen that the reaction temperatures of the K91 HG-CE thermal paper according to the respective gray scales reacted in a pattern similar to a linear function.

Previous research has shown that the epidermis breaks down and is rapidly thermally saturated when heat applied to the skin exceeds a temperature of 51° C. Also, it is known that the denaturization of collagen constituting most of connective tissues underneath the dermis shows the best correlation with an extent of burning. It has been reported that the above-described collagen fibers do not significantly break down at 57° C., but start to be cut at 60° C., and are structurally denatured at 65° C. Therefore, since the thermal paper started to react at 56° C., the initiation of the thermal reaction may be used to estimate that a burn is proceeding into the dermis and to determine the depth of the burn. Therefore, it could be seen that the thermal paper was suitable for a burning model since the thermal paper exhibited a thermal reaction from the temperature at a stage of early tissue reaction caused by the burn.

Meanwhile, the number of sheets of the thermal paper 11 stacked on the stacking member 10 is determined using a method of estimating an extent of thermal damage, or a method of deducing the number. In the case of standardization, the thermal paper 11 may be stacked in different numbers of sheets corresponding to standard tissues (classified according to certain parts in the skin). Adhesive oil 12 may also be applied between the stacked thermal paper 11 to improve thermal conductivity. The adhesive oil 12 serves to closely adhere the thermal paper 11. In this case, oil or thermal grease may be used as the adhesive oil 12. In a method of pressing the thermal paper 11 to closely adhere the thermal paper 11 with no gaps, the adhesive oil 12 may not be applied. Types of the adhesive oil 12 may widely vary according to the thermal conductivity of a targeted tissue. In this case, any materials that can enhance close adhesion strength to improve thermal conductivity may be used as the adhesive oil 12.

Reference holes 11a are formed through the stacking member 10 to form reference points upon 3D modeling. The reference holes 11a are formed on the same vertical line. Preferably, the two reference holes 11a are formed at a predetermined interval. In this case, the two or more reference holes 11a may also be formed.

The upper plate 30 is formed in a flat shape. The upper plate 30 is preferably made of a heat-resistant silicone material. An object of manufacturing the upper plate 30 is to reflect a similar temperature to that of a surface in which heat is intended to be measured, such as the skin, in the thermal paper. This is realized by heating the upper plate 30 to a temperature similar to a surface temperature of the skin, and then piling the stacked thermal paper 11 on the upper plate 30 to reflect the actual surface temperature of the skin, and thus the upper plate made of a silicone material is preferably added to realize such an object. Therefore, the upper plate 30 is preferably formed of a heat-resistant silicone material so that conditions similar to those of the skin can be recreated near the thermal paper 11. When the upper plate 30 is heated in hot water and dried to remove moisture, and the stacking member 10 is arranged on the upper plate 30, the stacking member 10 may be maintained at a temperature similar to that of the skin, thereby improving accuracy of the experimental results.

A lower plate 40 on which the upper plate 30 is placed is formed in a flat shape. The lower plate 40 is made of a plastically deformable metal material, preferably stainless steel. The lower plate 40 is preferably made of stainless steel capable of maintaining in a curved state similar to a shape of a subject to be measured when measurement of a curved surface rather than a flat surface is required. The upper plate 30 is attached to a top surface of the lower plate 40 in a state in which the shape of the lower plate 40 is deformed. In this case, the lower plate 40 is attached to the upper plate 30 using a double-sided adhesive tape. An adhesive other than the double-sided adhesive tape may also be used. Also, the two members may be attached to each other using a separate coupling member such as a bolt.

The pressing member 21 is made of a magnetic material. A neodymium magnet having a strong magnetic force is preferably used. When the pressing member 21 is placed on the stacking member 10 in a state in which the upper plate 30 and the stacking member 10 are placed on the lower plate 40 made of a metal material, a pressing force is applied to the stacking member 10 due to the magnetic force. In this case, gaps between the stacked sheets of thermal paper 11 are closely sealed due to the pressing force to prevent air from flowing through the gaps.

Also, the pressing member 22 may be formed as a clip or a band having an elastic force, as shown in FIG. 5. The pressing member 22 is formed so that both ends of the pressing member 22 are curved in the same direction to have an elastic force. In this case, when the stacking member 10 is between the ends of the pressing member 22, the thermal paper 11 constituting the stacking member 10 is closely adhered due to the elastic force of the pressing member 22 to prevent air from flowing through the gaps. When a clip or a band having a predetermined thickness is used as the pressing member 22, a groove into which the pressing member 22 may be press-fitted may be formed in the upper plate 30. Also, a clamp may also be applied as the pressing member 22. The clamp is generally a pressing device using a screw-driving method. In addition, a clip-shaped pressing member capable of clipping both of the upper plate 30 and the lower plate 40 to the stacking member 10 to smoothly transfer the heat of the upper plate 30 to the stacking member 10 may be applied.

Meanwhile, when none of the above-described pressing members 21 and 22 or a fixing device exist, a situation in which the highest contact layer is contracted upon contact with a high-temperature heat source was observed, but the heat transfer to the lower layers occurs easily with no great difficulty when there is no fixing device. When an adhesive serving as thermal grease is uniformly applied between the sheets of thermal paper 11 instead of the pressing members 21 and 22, the thermal grease closely adheres the thermal paper 11 to prevent air from flowing through the gaps between the sheets of thermal paper 11. Therefore, embodiments without the pressing member 22 are also possible. In this case, the thermal grease should have an adhesive force and heat stability such that close adhesion is maintained between the sheets of thermal paper 11 before heating and the thermal paper 11 may be easily separated without causing damage to thermal traces after heating. Also, since the thermal paper 11 may be stacked in a "Post-it" form when the adhesive oil 12 is used instead of the pressing members 21 and 22, it is possible to stack the thermal paper 11 on a desired curved surface, thereby widening its applicability. Also, after a test is performed on a surface layer, sheets of the thermal paper 11 with discoloration may be detached one by one, and the remaining thermal paper may be immediately re-used. Also, since the temperature may be checked according to the grayscale levels expressed for the thermal paper 11, it is possible to estimate the temperature with reference to the heat distribution obtained in this embodiment. Therefore, based on the heat transmission (the number of sheets of the thermal paper on which heat traces are formed) and heat distribution pattern (a heat distribution shape expressed by gray scales) obtained in this embodiment, a table capable of converting heat actually transferred to the tissue may be provided to enable immediate estimation of thermal conductive depth and distribution.

The method of measuring thermal conductivity using the apparatus for measuring thermal conductivity according to one embodiment of the present invention thus configured is as described below.

As shown in FIG. 7, the method of measuring thermal conductivity using the apparatus for measuring thermal conductivity includes a thermal paper stacking operation (S1), a preparation operation (S2), a heating operation (S3), and a thermal conductivity estimation operation (S4)/3D reconstitution operation (S5).

The thermal paper stacking operation (S1) is an operation of determining a number of stacked sheets of the thermal paper 11 constituting the stacking member 10 according to the thermal conductivity and thickness of a targeted tissue. The number of sheets of the thermal paper to be stacked is calculated using a method of deducing this number, which includes a thermal paper stacking operation that will be described below. In the case of standardization, the thermal paper 11 may be stacked in different numbers of sheets corresponding to standard tissues (tissues in parts of the skin). As shown in FIG. 2, the thermal paper 11 is stacked to form layers. In this case, types of the adhesive oil 12 may be determined and applied according to the thermal conductivity of the targeted tissue, or the stacking member 10 on which the thermal paper 11 is stacked in a state in which the adhesive oil 12 is applied onto the thermal paper 11 may be selected and tested.

When the thermal paper stacking operation (S1) is completed, a preparation operation (S2) of preparing the stacking member 10 to apply heat to a top surface of the stacking member 10 is performed.

The preparation operation (S2) includes an upper plate temperature regulation operation (S21) and a lower plate attachment/pressing operation (S22). The upper plate temperature regulation operation (S21) is an operation of regulating a temperature of an upper plate according to the temperature of the targeted tissue. When the targeted tissue is skin, the thermal paper may be maintained at a temperature similar to that of the skin by heating the upper plate 30 made of a heat-resistant silicone material in hot water, drying the upper plate 30 to remove moisture, and placing the upper plate 30 beneath the stacking member 10.

The lower plate 40 is attached to the upper plate 30 by means of an adhesive such as a double-sided adhesive tape. When the lower plate 40 is intended to be measured in a state in which a surface of the lower plate 40 is curved, the lower plate 40 is bent in a desired shape, and attached to the upper plate 30. In this case, the lower plate 40 may be made of a metal material capable of maintaining plastic deformation such that a deformed state is maintained. The pressing is performed using the pressing member 21 so that the stacking member 10 is fixed in the upper plate 30 and the lower plate 40 and the gaps between the sheets of thermal paper 11 in the stacking member 10 are closely sealed at the same time.

When the preparation operation (S2) is completed, the heating operation (S3) of applying heat from a heat source to be tested to a predetermined region of the top surface of the stacking member 10 is performed.

After heat is applied to the top surface of the stacking member 10 in the heating operation (S3), a 3D reconstitution operation (S5) of three-dimensionally reconstituting thermal images formed on the thermal paper piled as the respective layers of the stacking member 10 is performed. In this case, the thermal images formed on the thermal paper piled as the respective layers of the stacking member 10 are scanned and input into a computer. Then, the thermal paper 11 images may be sequentially stacked and reconstituted based on the reference holes 11a passing through the stacking member 10 to three-dimensionally reconstitute the thermal images formed in the stacking member 10.

When the heating operation (S3) is completed, the thermal conductivity estimation operation (S4) and the 3D reconstitution operation (S5) are performed at the same time or sequentially. The thermal conductivity estimation operation (S4) may also be performed while performing the 3D reconstitution operation (S5).

The thermal conductivity estimation operation (S4) is an operation of estimating thermal conductivity in a targeted tissue by converting an extent of thermal damage (i.e., a change in color of the thermal paper) according to the thermal depth of the stacked thermal paper 11 into a extent of thermal damage according to the depth of the targeted tissue.

As shown in FIG. 6, the extent of damage of the thermal paper according to the depth of the stacked thermal paper as shown in the left panel of FIG. 6 is converted into the extent of damage of the targeted tissue (i.e., the dermis of the skin) according to the depth of the targeted tissue as shown in the right panel of FIG. 6.

First, assuming that a subject to be tested in this experiment is made of a homogenous material and has a one-dimensional geometric structure, the subject satisfies the requirement that it have the same total quantity of heat when heat is applied to the same area (A) of the subject. That is, the subject satisfies the following Equation 1.

$$\Delta Q/\Delta t = -k A \times \Delta T/\Delta x \qquad \text{Equation 1}$$

Therefore, the total quantity of heat of the thermal paper is identical to the total quantity of heat of the skin. That is, the following Equation 2 is established.

$$-kp \times A \times (\Delta T/\Delta x\text{paper}) = -kd \times A(\Delta T/\Delta x\text{dermis}) \qquad \text{Equation 2}$$

wherein A represents a cross-sectional area, and ΔT represents a difference in temperature between both ends of the subject. In this case, when both sides of the subject are the same, A and ΔT may be omitted. Also, kp represents a thermal conductivity constant of the thermal paper, kd represents a thermal conductivity constant of the tissue, Δxpaper represents a depth of the stacking member, and Δxdermis represents a depth of the dermis of the skin.

When it is assumed that the same total quantity of heat reaches an area (A) of the final lower end, the quantity of heat reaching a lower portion of the dermis due to the burn is calculated so that the quantity of heat remains constant until several sheets of the thermal paper are stacked. The number of stacked sheets of the thermal paper thus calculated may be used to simulate depths of the skin to which the same quantity of heat is transferred. That is, points having the same total quantity of heat are calculated.

When a calculation is performed according to the following equation, since the difference in temperature between both ends of the subject is the same as the cross-sectional area in Equation 2, the depth of the stacked thermal paper having the same quantity of heat as the lowest layer of the skin is calculated:

$$\Delta x\text{paper} = \Delta x\text{dermis}(kp/kd) \qquad \text{Equation}$$

wherein Δxpaper represents the product of the number of sheets and the thickness of the thermal paper, that is, Number of stacked sheets of thermal paper=Δxdermis×(kp/kd)/Xd wherein Xd represents a thickness one sheet of the thermal paper.

That is, in the thermal paper stacking operation (S1), the number of stacked sheets of the thermal paper satisfies the relationship according to the following equation:

Number of stacked sheets of thermal paper=thickness of tissue×(kp/kd)/Xd  Equation Also, in the thermal conductivity estimation operation (S4), the thermal damage depth of the targeted tissue satisfies the relationship according to the following equation:

Thermal damage depth of targeted tissue=number of sheets of thermal paper with discoloration×Xd×(kd/kp),  Equation By way of example, a stacking model for the thermal paper having the same quantity of heat as the quantity of heat reaching the bottom of the skin in a rat having a skin thickness of 1.52 mm is calculated as follows.

The number of sheets may be calculated to be 8.7740 when:

$kd = 0.351691$ W/mK, $kp = 0.17$ W/mK,

Δxdermis=1.52 mm, and $Xd = 0.08374$ mm.

That is, it can be seen that it is necessary to stack approximately 9 sheets of thermal paper in the stacking model for the thermal paper having the same quantity of heat as the quantity of heat reaching the bottom of the skin in a rat having a skin thickness of 1.52 mm.

Also, the 3D reconstitution operation (S5) is an operation of three-dimensionally reconstituting thermal images formed in the stacking member 10 by imaging discolored portions of the thermal paper 11, which constitute the stacking member 10 undergoing the heating operation, sequentially from above, or scanning the thermal paper 11 and then stacking and reconstituting the images based on the reference holes 11a.

Then, the stacked images may be converted into the form of a temperature distribution according to the depth of the targeted tissue (i.e., skin) obtained in the thermal conductivity estimation operation (S4) to three-dimensionally model the stacked images into the form of a temperature distribution by heat conduction according to the total depth of the skin, that is, an extent of damage due to heat.

When it is assumed that the skin is scalded by hot oil, the apparatus and method according to one embodiment of the present invention may be used to simulate a burn caused by a hot flowing fluid. Particularly, the burn caused by such a fluid is very difficult to estimate using mathematical methods known in the related art since it is very complicated to simulate the fluid itself using a computer. On the other hand, the method according to one embodiment of the present invention may be easily applied to estimate the heat transfer and burns caused by solids, liquids and gases since the model itself is very simple.

Such an apparatus for measuring thermal conductivity may be used to develop burn protection equipment. When heat is applied onto a tissue of the burn protection equipment in a state in which the tissue is placed on the stacking member 10, it may be determined how safe the burn protection equipment is by checking whether an extent of thermal damage occurs in the stacking member 10 when a predetermined level of heat is applied to the tissue of the burn protection equipment.

The present invention has been described in detail. However, it should be understood that the detailed description and specific examples, while indicating embodiments of the invention, are given by way of illustration only, and various changes and modifications within the spirit and scope of the invention will become apparent to those skilled in the art from this detailed description.

The invention claimed is:

1. An apparatus comprising:
   a plurality of sheets of thermal paper;
   a thermal paper stacking member having the thermal paper stacked thereon to form layers; and
   a plate having the stacking member loaded thereon,
   wherein the apparatus is able to measure an extent of burning in a state in which the thermal paper is stacked, wherein adhesive oil is interposed between the stacked thermal paper sheets.

2. The apparatus of claim 1, further comprising a pressing member configured to press the thermal paper stacking member so that the plurality of thermal paper sheets are stacked and maintained in a closely adhered state.

3. The apparatus of claim 1, wherein the plate is made of a heat-resistant silicone material.

4. The apparatus of claim 3, wherein the plate is formed on a plastically deformable lower plate.

5. The apparatus of claim 1, wherein the adhesive oil is at least one selected from the group consisting of oil and thermal grease.

6. The apparatus of claim 2, wherein the pressing member is selected from the group consisting of a magnetic material, a clip, a band, and a clamp.

7. The apparatus of claim 1, wherein the stacking member has reference holes formed therethrough to form reference points for three-dimensional (3D) modeling.

8. A method comprising:
   a thermal paper stacking operation of determining a number of stacked sheets of thermal paper constituting a thermal paper stacking member according to thermal conductivity of a targeted tissue;
   a preparation operation of preparing the thermal paper stacking member having a plurality of thermal paper sheets and adhesive oil, wherein the adhesive oil is interposed between the stacked thermal paper sheets such that the thermal paper sheets closely adhere together, wherein upon application of heat, the thermal paper stacking member is configured to emulate a thermal distribution pattern into skin tissues;
   a heating operation of applying heat to be tested to a top surface of the stacking member; and
   a thermal conductivity estimation operation of estimating thermal conductivity in the tissue by converting an extent of thermal damage according to a thermal depth of the thermal paper piled as the respective layers of the stacking member into an extent of thermal damage according to a depth of the targeted tissue.

9. The method of claim 8, wherein the preparation operation comprises:
   an upper plate temperature regulation operation of regulating a temperature of an upper plate configured to be placed below the stacking member to maintain a temperature similar to that of the targeted tissue; and
   a lower plate attachment/pressing operation of, when measurement of a curved surface is required, plastically deforming a lower plate so that the lower plate has the curved surface and attaching the upper plate to the lower plate.

10. The method of claim 8, further comprising:
    a 3D reconstitution operation of three-dimensionally reconstituting a thermal image formed on the thermal paper piled as the respective layers of the stacking member after the heating operation of applying heat to be tested to the top surface of the stacking member.

11. The method of claim 8, wherein the number of stacked sheets of the thermal paper in the thermal paper stacking operation satisfies the relationship according to the following Equation:

$$\text{(Number of stacked sheets)} = \text{(Thickness of tissue)} \times (k_p/k_d)/X_d \qquad \text{Equation}$$

wherein "$k_p$" represents a thermal conductivity constant of the thermal paper,
"$k_d$" represents a thermal conductivity constant of the tissue, and
"$X_d$" represents a thickness of the thermal paper.

12. The method of claim 8, wherein the thermal damage depth of the targeted tissue in the thermal conductivity estimation operation satisfies the following Equation:

$$\text{(Thermal damage depth)} = \text{(Number of sheets of thermal paper with discoloration)} \times X_d \times (k_d/k_p), \qquad \text{Equation}$$

wherein "$k_p$" represents a thermal conductivity constant of the thermal paper,
"$k_d$" represents a thermal conductivity constant of the tissue, and
"$X_d$" represents a thickness of the thermal paper.

* * * * *